US005308359A

United States Patent [19]

Lossing

[11] Patent Number: 5,308,359

[45] Date of Patent: May 3, 1994

[54] APPARATUS AND METHOD FOR PRODUCING SPINAL DISTRACTION

[75] Inventor: Wallace W. Lossing, Fisherville, Va.

[73] Assignee: Lossing Orthopedic, Inc., Minneapolis, Minn.

[21] Appl. No.: 720,655

[22] Filed: Jun. 24, 1991

[51] Int. Cl.[5] .................... A61F 5/00

[52] U.S. Cl. .................... 606/242; 606/244; 606/245; 602/33; 602/34; 5/612; 5/613; 5/617

[58] Field of Search .................... 128/25 R, 70, 71, 74, 128/75; 269/322, 323, 324; 602/33, 34; 606/242, 244, 241, 32-36, 241-245; 5/610, 618, 612-614, 617, 662

[56] References Cited

U.S. PATENT DOCUMENTS

| | | | |
|---|---|---|---|
| 1,804,441 | 11/1930 | Silva | 606/244 |
| 2,907,324 | 5/1957 | Catanzaro | 602/34 |
| 3,015,330 | 1/1962 | Linstrom | 128/25 R |
| 3,293,667 | 12/1966 | Ohrberg | 269/323 |
| 3,450,132 | 6/1969 | Ragon et al. | 128/25 R |
| 3,751,028 | 8/1973 | Scheininger et al. | 269/322 |
| 4,002,165 | 1/1977 | Lind | 602/33 |
| 4,059,255 | 11/1977 | Perold | 269/323 |
| 4,345,344 | 8/1982 | Gadoury et al. | 5/610 |
| 4,362,151 | 12/1982 | Cottrell | 128/75 |
| 4,602,619 | 7/1986 | Wolf et al. | 128/75 |
| 4,660,549 | 4/1987 | Kowalski et al. | 606/242 |
| 4,664,101 | 5/1987 | Granberg | 128/84 R |
| 5,023,967 | 6/1991 | Ferrand | 5/618 |

FOREIGN PATENT DOCUMENTS

| | | | |
|---|---|---|---|
| 1181663 | 9/1985 | U.S.S.R. | 128/75 |

*Primary Examiner*—Richard J. Apley
*Assistant Examiner*—Jeanne M. Mollo
*Attorney, Agent, or Firm*—Moore & Hansen

[57] ABSTRACT

The present invention provides apparatus and method for therapeutically treating an injured spine by lifting and rotating the pelvic area to straighten the lumbar spine and by applying a force to the spine to separate vertebral bodies and to stretch the connective tissue along the spinal cord by relative movement of the body of the patient with reference to a fixed point.

44 Claims, 5 Drawing Sheets

APPARATUS AND METHOD FOR PRODUCING SPINAL DISTRACTION

The present invention relates to traction devices generally, and in particular to apparatus to provide distraction to selected regions of the human spine.

BACKGROUND OF THE PRESENT INVENTION

The application of a pulling or traction force directed substantially along the longitudinal axis of a human spine is a well known treatment method for providing therapeutic relief to an injured spine. Theoretically, traction provides curative action and relief from pain by stretching the tissue in the spinal column; by "decompressing" the spine to provide additional space between adjacent vertebrae and, consequently, increasing blood flow to the injured spinal vertebrae and tissue; by motion of the spinal vertebrae themselves; or by some combination of the foregoing. Typically, the traction force is applied to a patient who is resting in a supine or prone position on a bed. The traction force is applied by a device that utilizes weights that are suspended vertically from the end of a cord that runs over a pulley having a substantially horizontally disposed rotation axis. The other end of the cord is attached to the patient's body, sometimes to the patient's feet or to a harness surrounding the lower torso. Generally, the prior art traction devices each suffer from having several shortcomings that limit their effectiveness in treating spinal injuries.

First, many of these devices do not take into account the natural curvature of the spinal column, in particular the lumbar segment. The pull of the traction force they provide is directed generally along the axis of the spinal column, which due to this curvature prevents the force from providing the desired separation of the vertebrae.

Second, these devices typically are aimed at providing traction to either the lumbar or cervical regions of the spine, requiring two separate devices being needed to treat these separated spinal regions. Additionally, no known device is able to achieve the application of a traction force in the thoracic area of the spinal column, which lies between the lumbar and cervical areas.

Third, the applied traction force must overcome the frictional force existing between the bed surface and the patient's body. Because the frictional force is usually not accurately known, any accurate assessment of the actual traction force being applied to achieve the desired spinal stretching versus that spent overcoming frictional resistance between patient and bed surface is difficult to make.

Fourth, because of the inability to accurately assess the applied force used for stretching, it is difficult for a physician to know whether the patient is being properly treated. In other words, too little force may be applied to certain patients to achieve any therapeutic benefit and too great a force may be applied to other patients, potentially exacerbating their injuries.

Sixth, in the healing process, the connective tissue surrounding the injured area can bind and constrict. Nerve endings can be impinged upon with resulting pain. Binding and constriction of the connective tissue in one affected area can distort the connective tissue throughout the body. To reduce tissue binding and constriction, the tissue must be permanently plastically deformed. Many, if not all, of the prior art devices operate only in the elastic stress regime of the connective tissue of the spinal column, however. That is, this tissue, e.g., the durameter and the fascia, elastically stretches upon application of the traction force and elastically rebounds upon removal of the traction force. The tissue stretching—and consequent relief for the patient—is therefore of a temporary nature. To produce a permanent stretching and relief, a traction device must therefore safely operate in the tissue's plastic stress regime as well as its elastic.

As is well known, materials, including the connective tissue of the spinal column, exhibit both elastic and plastic qualities depending upon the stress to which they are subjected. On a stress/strain curve the point at which the material begins to exhibit plastic rather than elastic properties is known as the material's yield point. By applying a force to the connective tissue of the spinal column sufficient to stress the tissue past its yield point, a permanent rather than temporary stretching of the tissue may be achieved. Such a yielding of the spinal tissue can only be accomplished in a safe and therapeutic manner if the exact amount of traction force being applied to the spinal column is known with certainty, which is not the case in prior art devices. As noted, if the stress applied to a material is in the elastic region, and thus below the yield point of the material, the material will elastically deform and upon removal of the stress will return to substantially the same configuration and structure as it had prior to the application of the stress. Applying a stress greater than the material's yield point, however, will result in a permanent deformation of the material. Permanent stretching of the connective tissue would ease the compressive pressure felt along the spinal column and will promote healing thereof. Thus, in a treatment where it is desirable to reduce binding and constriction of the connective tissue and to increase the spacing between the individual vertebra, it would be desirable to generate a distraction force to separate the vertebrae and to safely stress the connective tissue of the spine beyond its yield point to achieve a permanent stretching thereof.

Finally, the known traction devices often require considerable bending and movement of the patient's body to get into a proper position for the beginning of therapy. For many patients, any bending can be difficult and painful and is therefore to be avoided during a therapy session if possible.

Some newer traction devices attempt to compensate for such deficiencies just listed. For example U.S. Pat. No. 4,602,619 to Wolf et al. teaches an apparatus and method for applying varying amounts of traction to the spine at an angle to the elongated axis thereof. The apparatus includes a harness placed around and upwardly supporting the patient's pelvic region. A cable is attached at one end to the harness and leads through a pulley attached to an overhead support. The cable may be anchored by means of a cleat attached to the pulley. The overhead support includes a rearwardly and downwardly extending arm connected to an electric screw actuator. In use, the patient pulls on the free end of the cable, thereby raising his pelvic region and substantially simultaneously rotating it. The cable is then anchored and by engaging the actuator, the harness pulley may be moved upwardly and forwardly and then downwardly and rearwardly in alternation to provide a varying amount and direction of force to stretch the spine and to promote healing of damaged spinal areas, particularly in the lumbar area. The patent also makes non-specific claims to being able to treat other portions of the spine with the device.

Thus, a need exists for a traction device that is capable of providing a traction force of known amounts to selected, specific spinal portions. Such a device should be able to carefully and progressively stress the connective tissues of the spinal column into the plastic regime thereof to obtain a permanent stretching of the connective tissue, thereby increasing the space between the individual vertebra.

OBJECTS OF THE PRESENT INVENTION

It is a principal object of the present invention to provide new and improved apparatus that is not subject to the foregoing disadvantages.

It is another object of the present invention to provide apparatus capable of applying traction to the lumbar, thoracic, and cervical regions of the spine.

It is yet another embodiment of the present invention to provide apparatus capable of applying a traction force to the spine of a human being to provide permanent relief by safely and therapeutically stressing the connective spinal tissue into its plastic stress region to achieve a permanent stretching thereof.

It is still another object of the present invention to provide apparatus that provides a known amount of traction force to an isolated spinal area.

It is still yet another object of the present invention to provide an apparatus that minimizes the bending and movement that a patient must undergo to be properly positioned for a therapy session.

It is yet another object of the present invention to provide an apparatus capable of positioning a human being in a 90/90 position for distraction with a minimum of effort on the patients behalf.

It is yet another object of the present invention to provide apparatus for applying traction to the spine of a human being through the use of the patient's own body weight.

SUMMARY OF THE PRESENT INVENTION

The foregoing objects of the present invention are achieved by apparatus that produces a distraction force on an isolated injured spine area by the relative movement of particular portions of the body. The apparatus provides a slow increase in the applied distraction force up to a preselected maximum that stresses the connective tissue of the spine into its plastic response region. The distraction force sufficiently stresses the tissue so as to achieve a permanent deformation thereof and to provide a therapeutic increase in the spacing of the individual vertebra forming the human spinal column.

An embodiment of the present invention includes a bed having torso and leg portions. The leg portion is elevatable and forwardly translatable. The torso portion is pivotable to prevent anterior wedging of the vertebrae when the pelvic region is subsequently rotated. The torso portion is pivotable to an angle of approximately 15 degrees with respect to a horizontal axis disposed approximately one and one-half inches below the lumbar-sacral joint of a properly positioned patient. Together the leg and torso portions properly dispose a patient in a 90/90 position wherein the patient's spine and femur are disposed at about ninety degrees to each other and the patient's femur and tibia are disposed at about ninety degrees. The forward translation of the leg portion places the buttocks closer to the foot of the bed than the knees are. Overhead support means for lifting the pelvic region of the patient's body approximately one-half inch off the bed, for rotating the pelvic region and straightening the lumbar spine, and for providing a fixed point of reference is provided. The overhead support means lifts the patient's pelvic area by means of a cord attached to the pelvis-encircling harness in the crotch area thereof and supports a static weight as a result. A slight rearwardly directed lift by the harness rotates the pelvis and straightens the lumbar spine to place the patient in a 90/90 position for distraction. The torso portion of the bed and overhead support means are relatively movable so as to achieve a progressive, selected transference of upper body weight to the overhead support means in addition to that static weight provided as a result of elevating the pelvic area, thereby resulting in a distraction force applied to the lumbar spine area. A desirable range of force is in the area of about two to about twelve pounds.

The weight transference and consequent application of the distraction force results from a slow initially downward and rearward movement of the bed at an angle of about 9½ degrees with respect to a horizontal axis for a total horizontal displacement of approximately 4½ inches, and a subsequent upward/rearward movement of the bed at about a 14½ degree angle for an additional horizontal rearward displacement of a maximum of a approximately 10 inches.

In another embodiment of the present invention, lumbar spine traction is provided by movement of the overhead support means along a similar but reversed and inverted path relative to that followed by the movement of the bed as previously described.

The present invention may include instrumentation means for initially determining the weight of the elevated pelvic region and continuously determining the weight of the elevated region as the bed is lowered. Means for discontinuing the relative movement when the total weight of the elevated area equals the initial weight plus the desired traction force is included. The instrumentation means provides for a continuous monitoring of the known traction force as it is slowly applied by the relative movement of the bed and support means. As the maximum desired traction force is reached, relative motion ceases. The connective tissue of the spinal column warms as fluid flows between the separated vertebrae and stretches slowly, consequently transferring upper body weight back to the bed. When the instrumentation means indicates that it is once again supporting the initial pelvic weight, relative movement again begins and continues until the maximum desired distraction force is once again achieved. This alternate application of distraction force may be continued in the discretion of the therapist to achieve a permanent, therapeutic stretching of connective tissue.

Another embodiment of the present invention includes means for applying traction to the cervical region of the spine. This embodiment includes means for restraining the cervical region with a cervical collar attached to an overhead support means located at the head of the bed.

Thoracic traction as achieved by the present apparatus by restraining both pelvic and cervical regions as previously described and providing the relative movement between the bed upon which the patient rests and the overhead support means.

In a desirable embodiment, the apparatus of the present invention may include a bed pivotable about a horizontal axis to facilitate ease of access to the therapeutic table by an injured person. In such an embodiment, the therapeutic table of the present invention would include a foot rest extending substantially vertically with respect to the horizontal bed. When the bed is pivoted upwardly about its horizontal axis, the foot rest is disposed near the floor and provides a means for the patient to step onto and lean against the bed. The bed may then be lowered back to the horizontal and the patient may be placed into the 90/90 position for distraction and the beginning of the therapy.

The foregoing objects and advantages of the invention will become apparent to those skilled in the art when the following detailed description of the invention is read in conjunction with the accompanying drawings and claims. Throughout the drawings, like numerals refer to similar or identical parts.

DETAILED DESCRIPTION OF THE INVENTION

Figure 3:
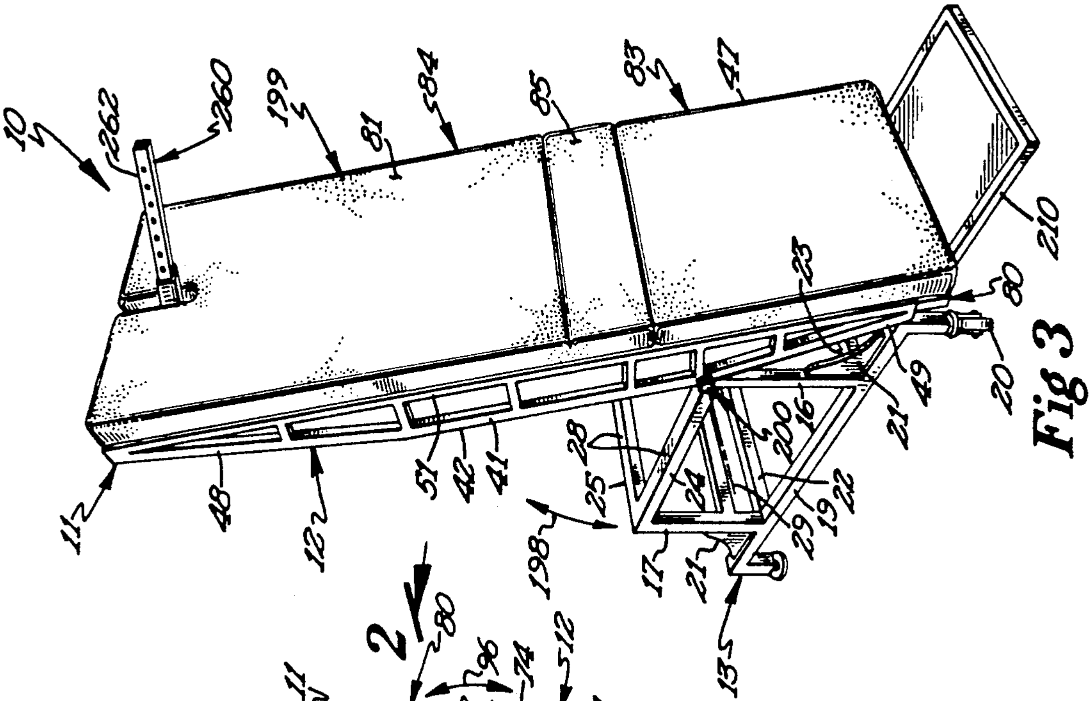
FIG. 3 is a perspective view of the table shown in FIG. 1 with the patient bed pivoted to a patient access position.
Figure 1:
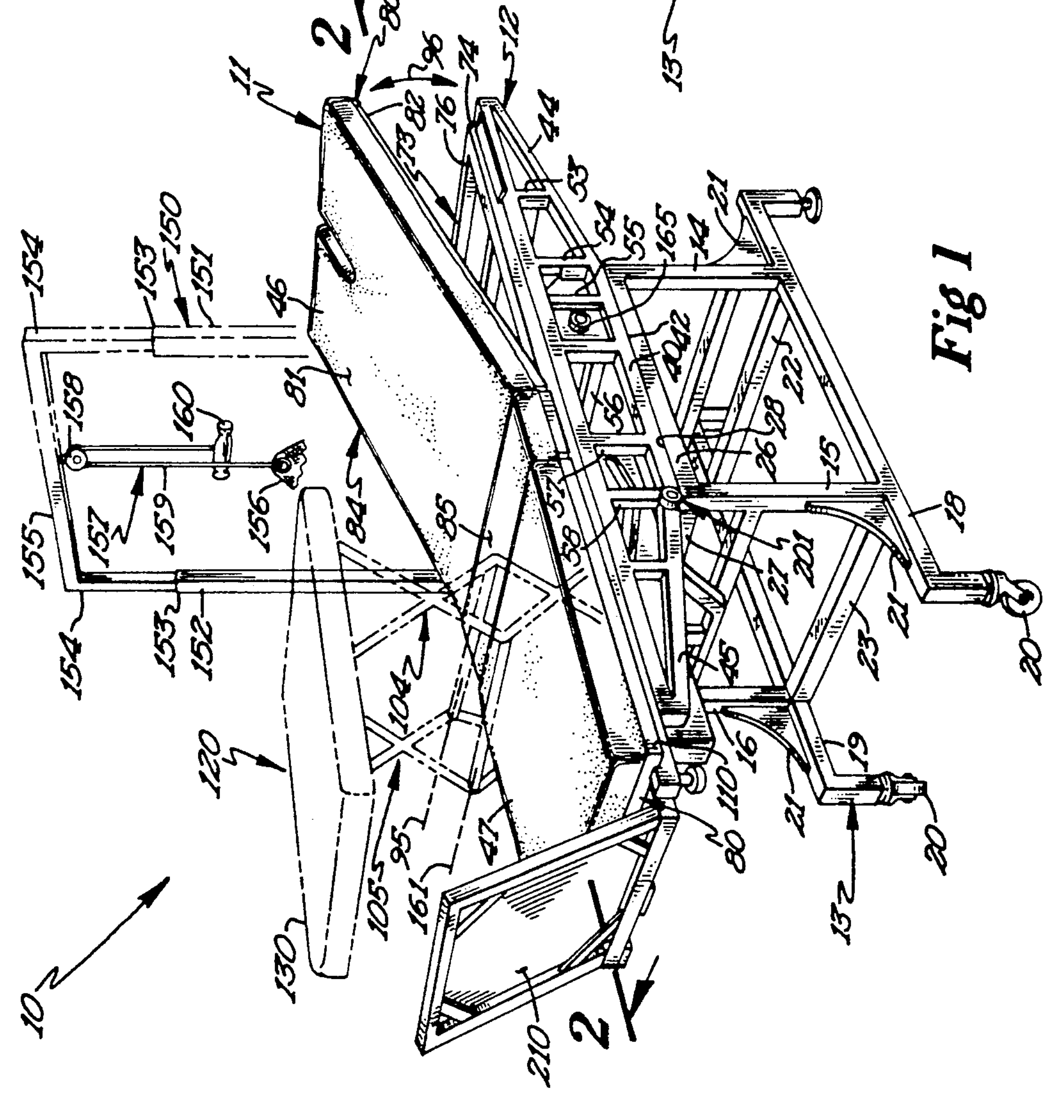
FIG. 1 is a perspective view of an embodiment of a distraction table in accord with the present invention showing the torso portion of the bed raised to an operative position and showing the lower leg portion in phantom raised to an operative position.
Figure 2:
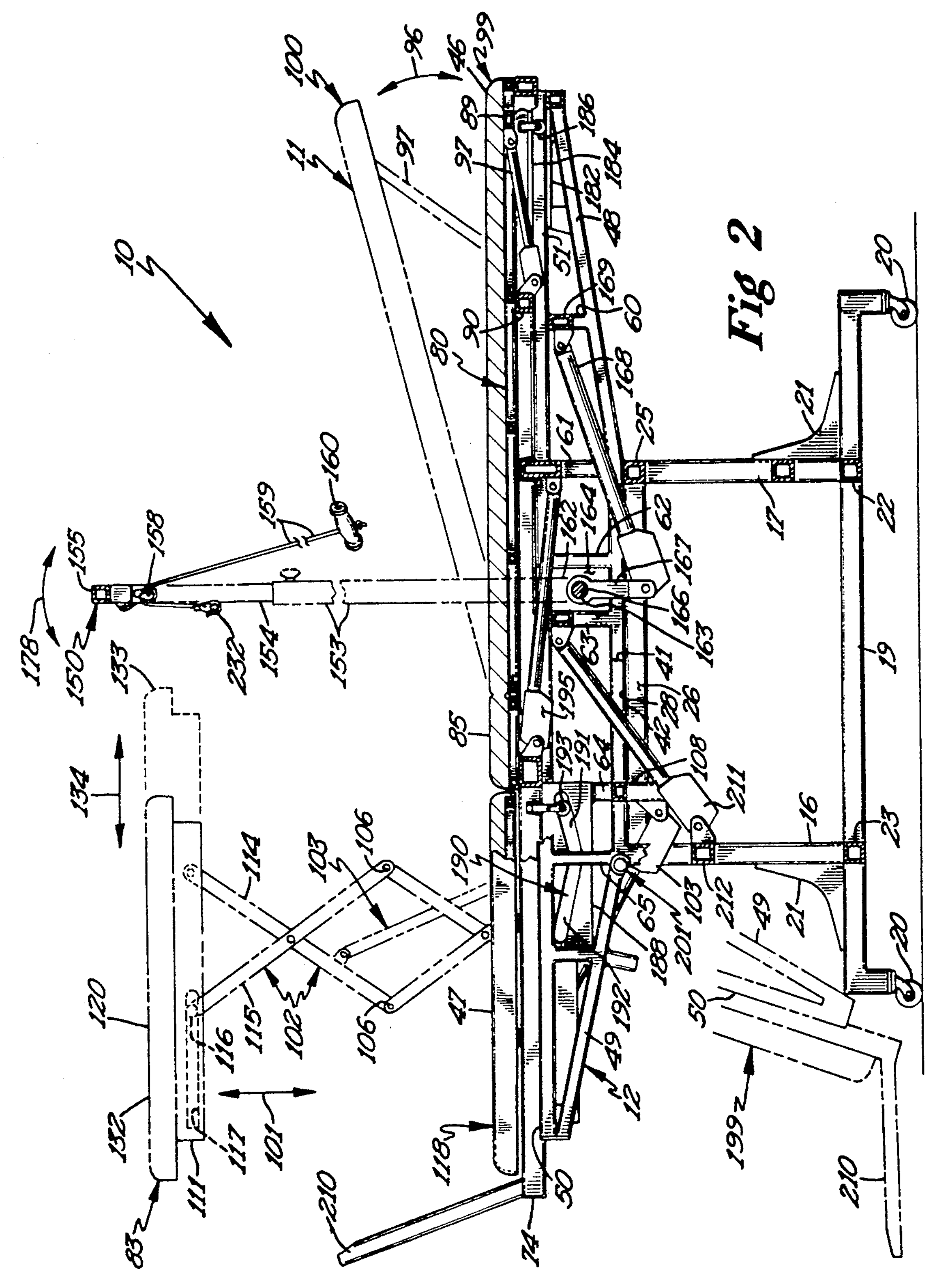
FIG. 2 is a cross-sectional view of the table shown in FIG. 1 taken along cutting plane 2—2 thereof and showing the torso portion of the table raised to an operative position in phantom and the lower leg portion in phantom raised to an operative position.

FIGS. 1–3 illustrate a therapeutic distraction table 10 in accordance with the present invention. Distraction table 10 includes a bed 11 movably supported by a carriage means 12, which is in turn supported by a supporting base means 13. Supporting base means 13 may take the general form of a four-pedestal frame as shown. Thus, supporting base means 13 includes pedestals 14–17 arranged in a substantially rectangular configuration. The pedestals 14–17 are mounted to and extend generally upright from a pair of elongate, substantially parallel longitudinally extending base rails 18 and 19. Distraction table 10 may be supported for movement of distraction table 10 by caster wheels 20 and may include brakes to inhibit unwanted motion of distraction table 10 during use thereof. Gussets 21 extend between the pedestals and rails 18 and 19 to provide additional upright support for the pedestals. Thus, for example, a gusset 21 extends between pedestal 14 and rail 18. Supporting base means 13 may also include transverse base rails 22 and 23 extending between elongate rails 18 and 19. Pedestal supporting rails 24–26 and pedestal supporting structure 27 (best seen in FIG. 5) extend between the tops of pedestals 14–17 to provide a substantially rectangular top support structure for base means 13 as well as a strong and sturdy base for carriage means 12. Pedestal support rails 24–26 and pedestal support structure 27, to be discussed in more detail below, each include a top surface 28 that partially serves as a rest for carriage means 12, which is pivotally attached to supporting base means 13 along a pivot axis 29, best seen in FIG. 3.

As previously noted, distraction table 10 may, if desired, include supporting base means 13 to which carriage means 12 is pivotally attached. The use of supporting base means 13 and its attached caster wheels 20 allows distraction table 10 to be readily moved from one location to another as desired. Where distraction table 10 is to be permanently located, supporting base means 13 may be dispensed with and carriage means 12 may be pivotally attached to a permanent supporting structure.

Figure 4:
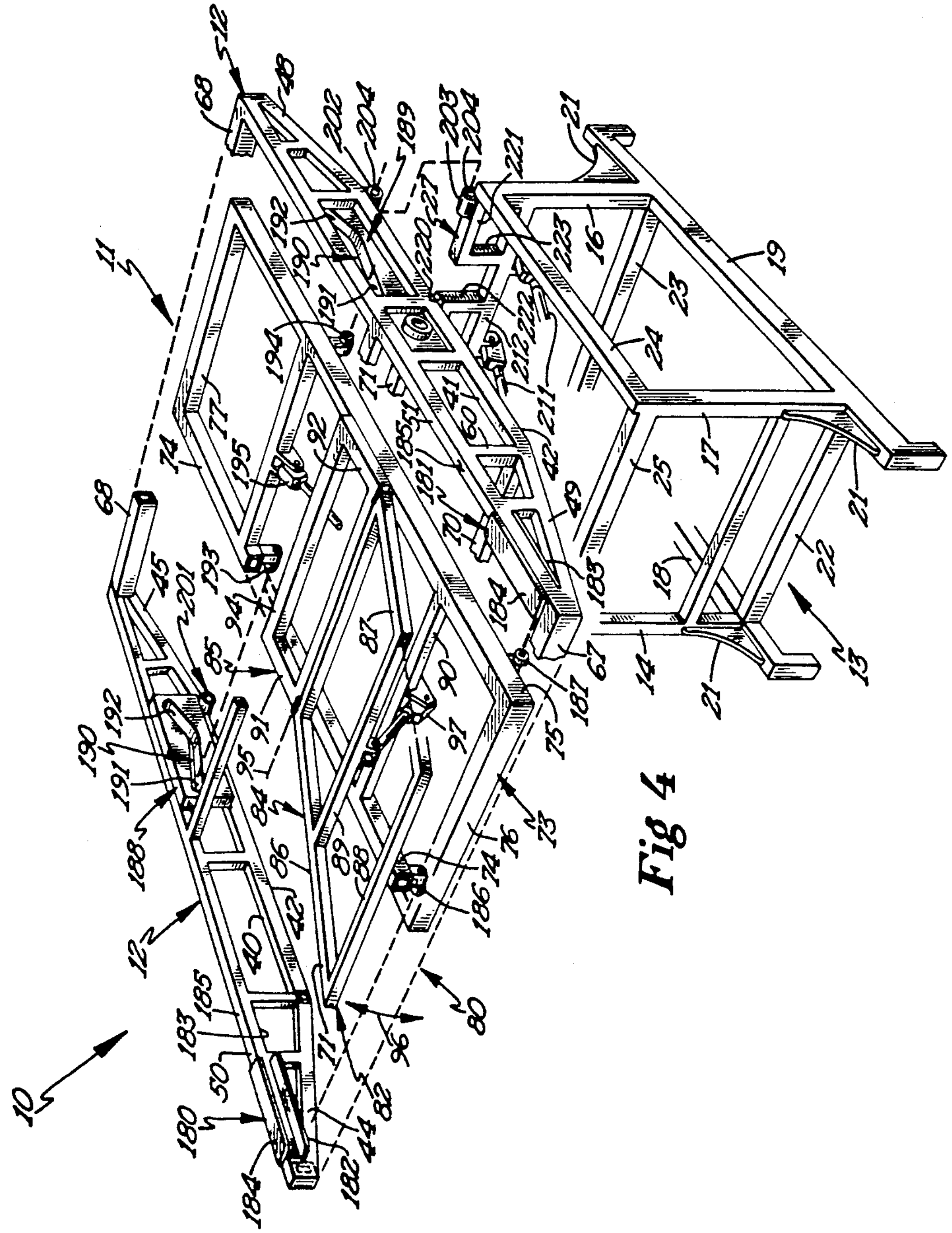
FIG. 4 shows the table of FIG. 1 with the bed cushion removed to illustrate in an exploded perspective view some of the structural elements of the table and the pivotal connections between relatively pivotable elements.

Carriage means 12 includes longitudinally extending carriage base rails 40 and 41 each having a bottom surface 42 that rests in part upon top surfaces 28 of carriage support rails 24 and 26, respectively. Carriage means 12 further includes diagonal rails 44 and 45 extending longitudinally away from base rail 40 towards the head 46 and foot 47 of the distraction table 10, respectively. Similarly, a pair of diagonal rails 48 and 49 extend longitudinally away from carriage base rail 41 to the head and foot of distraction table 10, respectively. A pair of bed support rails 50 and 51 extend the entire length of distraction table 10 and are attached to the free ends of diagonal rails 44, 45 and 48, 49, respectively. Rail group 40, 44, 45 and 50 and rail group 41, 48, 49 and 51 have a substantially inverted triangular frustum configuration. A plurality of generally upright bracing rails 53-59 extend between bed support rail 50 at the top and rails 40, 44, and 45 at the bottom, while a similar plurality of rails 60-66 extend between bed support rail 51 at the top and rails 41, 48 and 49 at the bottom. While seven such rails are shown on each side, more or less are within the purview of the present invention so long as the apparatus is properly structurally supported against collapse and unwanted movement of any kind. Additional structural support is provided by a plurality of carriage transverse support rails. Thus, as best seen in FIG. 4, rails 67, 68, and 69 extend between rails 50 and 51 at the head, middle, and foot of carriage means 12 and rails 70 and 71 extend between rails 40 and 41. Additional or less cross-bracing structural support can be used as desired so long as the mechanical movements of the distraction table 10 are not impeded and the table 10 does not become structurally unsound or subject to wiggling or swaying.

Figure 5:
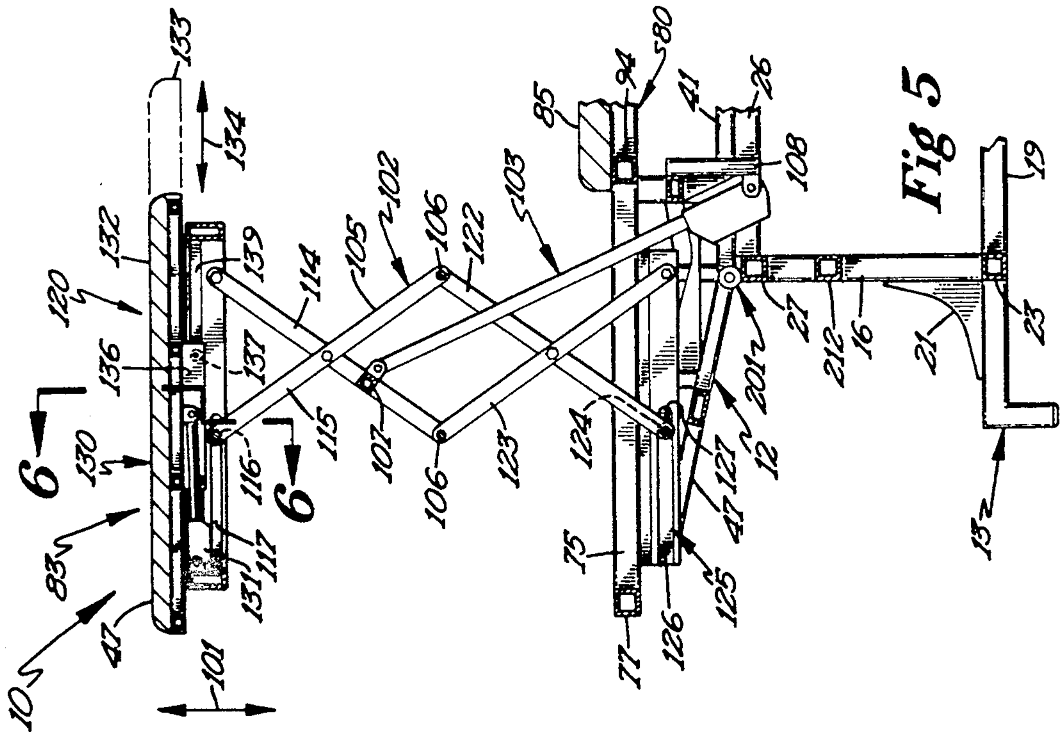
FIG. 5 depicts the lower leg portion of the table in FIG. 1 in a raised position and shows in phantom the stool forwardly translated into an operative position.

Carriage means 12 movably supports a bed 11. Referring principally to FIG. 5, now, bed 11 includes an elongate rectangular subframe 73 having longitudinally extending side rails 74 and 75 and transverse head and foot rails 76 and 77 extending between side rails 74 and 75 at the head 45 and the foot 46 of bed 11, respectively. Additional transverse rail supports may be provided as desired. Bed subframe 73 underlies and supports a bed frame 80 that supports a cushioning means 81. Frame 80 includes an upper portion 82 (FIGS. 1, 4) for generally supporting the patient's torso region and a lower, elevatable portion 83 (FIG. 3) for generally supporting the patient's leg region. Upper bed frame portion 82 includes an upper torso portion or wedge 84 and a pelvic portion 85.

Upper torso portion 84 includes a pair of spaced apart, longitudinally extending side rails 86 and 87 and a plurality of transverse rails 88, 89, and 90 extending therebetween to underlie and support cushioning means 81. Pelvic portion 85 includes short side rails 91 and 92 and transverse rails 93 and 94 extending between the ends of rails 91 and 92 as best seen in FIG. 4. Lower pelvic portion 85 is fixed to frame 80 while upper torso portion 84 is pivotally attached to lower pelvic portion 85 about a pivot axis 95 and may be pivoted thereabout as indicated by double-headed arrow 96, best seen in FIG. 2. Pivot axis 95 between upper portion 84 and pelvic portion 85 should be generally located just below where the lumbosacral junction of the patient would be located. Thus, the hinge between bed portions 84 and 85 should be about one to one and one half inch below the lumbosacral junction. Pivoting of upper torso portion 84 is achieved by an actuation means 97 (FIG. 2) attached at one end to upper torso portion 84 at transverse rail 89 and at the other end to transverse support rail 98 of bed subframe 70. Actuator means 97 and the other actuators used with table 10 will be discussed in more detail below. Upper torso portion 84 is thereby pivotable between a first, or substantially horizontal position 99, shown in solid lines in FIG. 2, to a second, angled position 100 shown in solid lines in FIG. 1 and in phantom in FIG. 2. Pivoting of upper torso portion 84 to position 100 for therapy is desirable to prevent the spine from being forces into flexion, resulting in anterior wedging of the vertebral bodies of the spine. Anterior wedging occurs when the spine is forcibly elongated or over-straightened such that the anterior or inward facing portions of the spinal vertebrae are forced into near or actual contact with each other. Such wedging can be harmful to a patient and can aggravate an existing injury.

Elevatable portion 83 of bed frame 80 and its elevating mechanism will now be described. As noted, portion 83 generally supports the legs of a patient in an elevated position relative to the remainder of his body, i.e., in the 90/90 position wherein the lower leg forms a substantially 90 degree angle with the upper leg and the upper leg forms a substantially 90 degree angle with the spine. Portion 83 may be variably elevatable to accommodate patients of different sizes, as indicated by double-headed arrow 101 (FIGS. 2, 5). As shown in FIGS. 1, 2 and 4, leg portion 83 is variably elevatable in a substantially perpendicular direction relative to bed 11. A parallelogram linkage 102 that is extendable by an actuator means 103 is used to elevate portion 83. As best seen in FIG. 1, parallelogram linkage 102 comprises substantially identical side linkages 104 and 105 having cross-members 106 extending therebetween for support and to tie the linkages together. Actuator means 103, which may be of the same type as means 97, is pivotally attached at one end to a cross member 107 and at the other end to carriage means 12 at a downwardly depending member 108 thereof.

Elevatable portion 83 includes a supporting base structure comprising a pair of spaced apart, longitudinally extending side rails 110 (FIG. 1) and 111 (FIG. 2) and transverse rails 112 and 113 extending between the ends of rails 110 and 111 as shown to provide a substantially rectangular base structure. Referring to FIG. 5, the upwardly most disposed links 114 and 115 of parallelogram linkage 102 are pivotally attached in a known manner to side rail 111. The attachment of link 115 includes a roller 116 disposed in a channel-track 117 formed in rail 111. Thus, in its unelevated position 118 shown in solid line in FIGS. 1 and 2, roller 116 would be disposed within track 117 at an end 119 thereof. When in an elevated position 120 such as that shown in phantom in FIGS. 1 and 2 and in solid lines in FIG. 5, roller 116 will have rolled within track 117 to near the other end 121 thereof.

Similarly, lower links 122 and 123 are pivotally attached at their lower ends in a known manner to carriage means 12. The attachment of link 123 includes a roller 124 disposed in a channel-track 125 attached to carriage 12. Thus, in its unelevated position 118 shown in solid line in FIGS. 1 and 2, roller 124 would be disposed within track 125 at an end 126 thereof. When in an elevated position 120 such as that shown in phantom in FIGS. 1 and 2 and in solid lines in FIG. 5, roller 124 will have rolled within track 125 to near the other end 127 thereof. Links 114 and 123 are pivotally attached to each other at one cross member 106 while links 115 and 122 are pivotally attached to each other at the other cross member 106.

It will be understood that the foregoing description of the attachment of linkage 105 between elevatable portion 83 and carriage means 12 similarly describes the attachment of linkage 104 therebetween. It will further be understood that parallelogram linkage 102 is but one known means of elevating lower portion 83 and that other such means, such as a single actuator means properly attached therebetween would also suffice.

To provide a 90/90 position for distraction it is desirable that the knees be moved slightly forward from a position where the lower and upper legs form an exact 90 degree angle. Thus, lower portion 83 includes a forwardly translatable stool 130 and an actuation means 131 for forward translation of stool from a retracted position 132 shown in phantom line in FIG. 2 and in solid line in FIG. 5 to an operative position 133 shown in dotted line in FIG. 2 and in phantom line in FIG. 5, as indicated by arrow 134 in FIG. 5.

Figure 6:
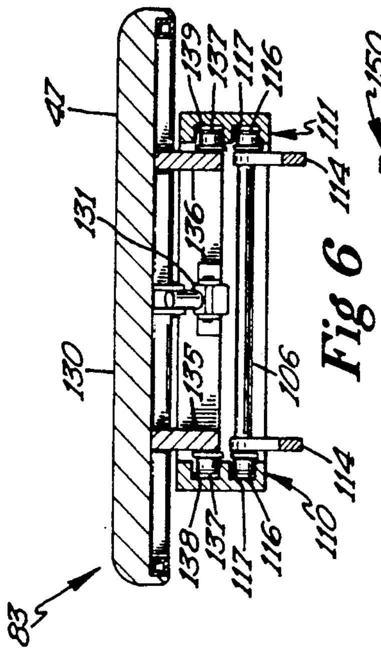
FIG. 6 in a cross-sectional view of the translating stool of the lower leg portion taken along cutting plane 6—6 of FIG. 5.

Referring now to FIG. 6, translatable stool 130 includes vertical rails 135 and 136 depending downwardly from cushioning means 81. Each vertical rail 135, 136 is mounted to its respective side rail 110, 111 by a pair of rollers 137 that roll within a track 138, 139, formed within side rail 110, 111, respectively. Actuation means 131 is extendable and retractable to provide a forward/rearward translation of stool 130 as rollers 137 roll in tracks 138 and 139.

Therapeutic distraction table 10 also includes a means for rotating and lifting 150 the pelvic region of a patient. Means 150 has an inverted Unshaped configuration and comprises a pair of pivotally attached, height-adjustable arms 151 and 152 each including relatively telescoping lower and upper members 153 and 154, respectively. Thus, members 154 are slidable within a bore formed within members 153 so as to be able to adjust the height of a cross-piece 155 extending between the members 154. Cross-piece 155 supports a harness 156 that is used to encircle, lift, and rotate a patient's pelvic region prior to beginning treatment to straighten the patients lumbar spine to complete the positioning of the patient for 90/90 distraction. A means for varying 157 the height of the harness relative to the bed 11 may be included and may be a cleat-type pulley 158 or the like over which a cord, rope, or the like 159 may be passed. Harness 156 is attached to one end of cord 159 and a handle 160 may be attached to the other end thereof. After a patient has been placed on bed 11 and harness 156 attached to cord 159, the patient or treating technician will pull on handle 166 to elevate the patient's pelvic region off of bed 11 a distance of about one-half inch, simultaneously rotating the pelvis to substantially straighten the lumbar spine. The cord can then be secured using known means such as a cleat on pulley 158. Harness 156, in particular, and means for lifting and rotating 150, in general, provide a fixed reference point relative to bed 11 and a patient situated thereon.

Preferably, means for lifting and rotating 110 is pivotally attached to carriage means 12 along a pivot axis 161. Pivoting allows means 150 of distraction table 10 to assume different angular relationships to bed 11 and thus to reach different portions of the patient's spine with the distraction provided by the present invention. Means 150 is pivotal through an arc of up to about 120 degrees as indicated by double-headed arrow 178 in FIG. 2. Referring to arm 152 and FIG. 2, the pivotal attachment of means 150 to table 10 will be described, it being understood that arm 151 is similarly attached. Thus, arm 152 has an end 162 that fixedly receives a transverse pivot shaft 163. Shaft 163 extends through a plate 164 having a bearing aperture 165 (best seen in FIG. 1). The end of shaft 163 internal of carriage means 12 is fixedly received within an aperture 166 transversely disposed in a lever arm 167. Means 150 is pivoted by an actuation means 168, best seen in FIG. 2, that is attached at one end to lever arm 167 and at the other end to a transverse support member 169 extending between upright members 53 and 60 of carriage means 12.

In the preferred embodiment bed 11 is, as a whole, substantially longitudinally translatable relative to bed subframe 73 to produce the distraction of the spine. Thus, distraction table 10 includes a means for producing a relative movement of bed 11 relative to means for lifting and rotating 150 generally and to cross-piece 155 in particular, which as noted, serves as a substantially fixed reference point relative to bed 11 and a to patient lying thereon. As best seen in FIG. 4, subframe 73 is movably mounted to carriage means 12 by means of a roller/track system. Thus, carriage means 12 includes a pair of substantially horizontally disposed tracks 180, 181 respectively attached to rails 50, 51. Each track 180, 181 comprises a Unshaped channel defined by a lower track plate 182 affixed by means such as welding to the lower surface 183 of rail 50 and 51 respectively; an upper track plate 184 also affixed by means such as welding to the upper surface 185 of rail 50 and 51 respectively; and by the inner surface 186 of rails 50 and 51 respectively. A pair of rollers 186 and 187 are respectively attached to longitudinally extending side rails 74 and 75 of bed subframe 73. Rollers 186 and 187 are received by tracks 180 and 181 respectively when subframe 73 is mounted to carriage means 12.

Figure 8:
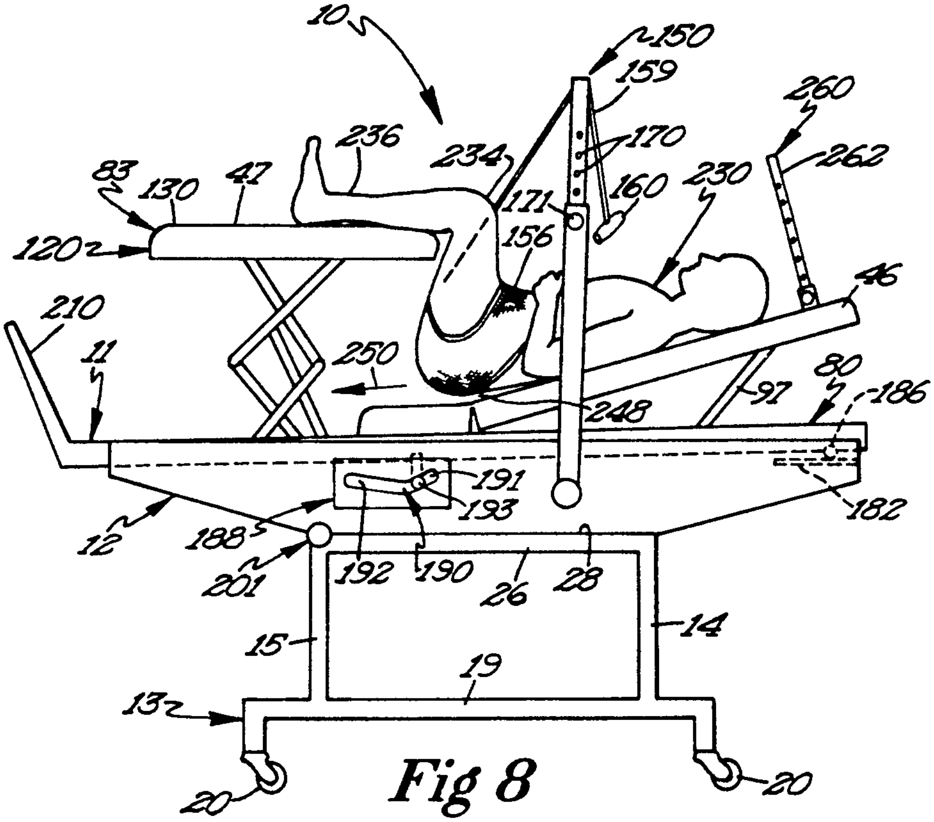
FIG. 8 is an operative, schematic view of a patient disposed on the table in an 90/90 position for distraction after the bed of the distraction table has been translated.
Figure 9:
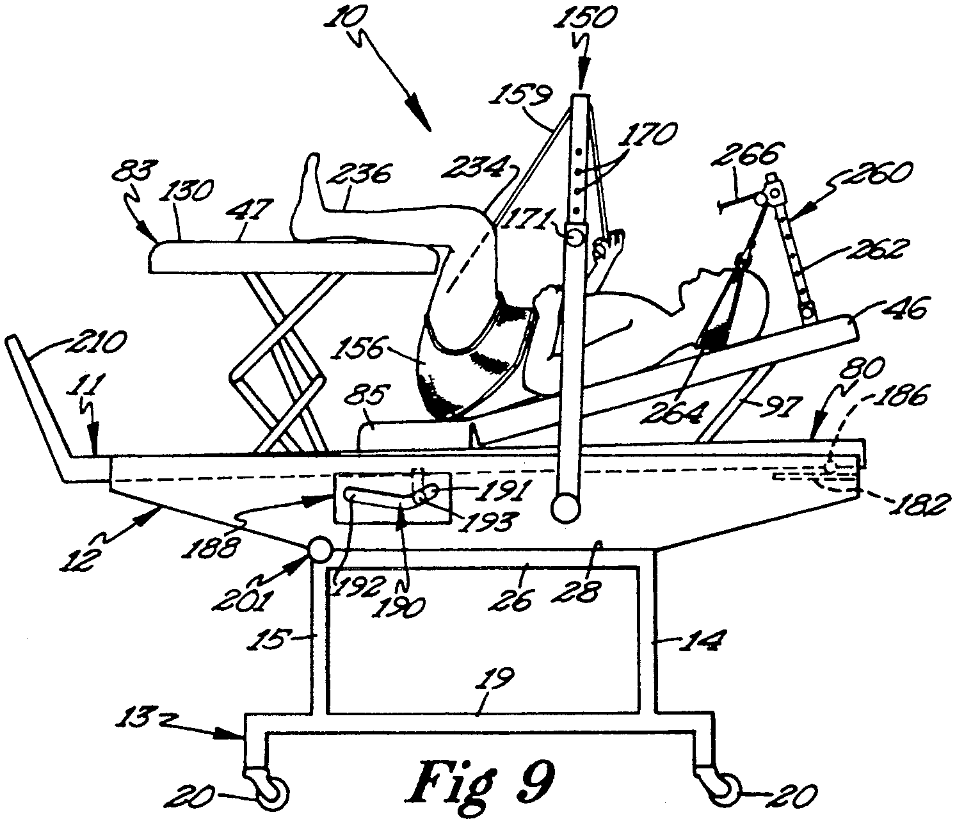
FIG. 9 is an operative, schematic view of a patient disposed on the table shown in FIG. 1 after the spinal tissue has plastically elongated following the translation of the bed shown in FIG. 8.

The height of cross-piece 155 relative to cushioning means 81 may be adjustable if desired. Thus, as best seen in FIGS. 8-9, upper arm members 154 may include a plurality of spaced apart holes 170 that receive a pin 171 insertable through a hole (not shown) in the lower arm member 153.

Subframe 73 is further mounted to carriage means 12 by a second roller/track system disposed more toward the foot of the bed. Thus, a pair of plates 188 and 189 are mounted to rail pairs 40, 50, and 41, 51. Each plate defines an internal angled force application path or track 190 having a first segment 191 that slopes downwardly toward the foot 47 of the table 10 and a second segment 192 that slopes upwardly from the first segment toward the foot 47 of the table 10. Track 190 of plate 188 receives a roller 193 rotatably attached to side rail 74 of subframe 73 while track 190 of plate 189 receives a roller 194 rotatably attached to side rail 75 of subframe 73. In a preferred embodiment of the present invention first segment 191 forms an angle of about 9½ degrees with respect to the horizontal and second path segment 192 is inclined upwardly from the low end of first segment 191 at an angle of about 14½ degrees with respect to the horizontal. The drop in height along first path segment 191 is about one and three quarter inches while the length is in the range of about four to five inches. The length of second path segment 192 should be less than about ten inches. Subframe 73 is moved along track 180, 181 and 190 by an actuation means 195 that is pivotally attached at one end to carriage means 12 and at the other end to bed subframe 73. Track 190 will be discussed in greater detail in the operational section below.

As noted earlier in the specification, many patients in need of therapy can bend and move only with some degree of pain and difficulty. To facilitate the use of distraction table 10 by these patients, carriage means 12, and thus bed 11, is pivotable about previously mentioned pivot axis 29 through an arc of about seventy degrees as indicated by arrow 198 such that bed 11 is disposed at an angle of about seventy degrees to the horizontal in a patient access position 199 as shown in FIG. 3. Thus, carriage means 12 is pivotally attached to supporting base means 13 at a pair of hinges 200 (FIG. 1) and 201 (FIG. 2). As best seen in FIG. 4, each hinge includes coaxial cylinders 202 and 203 respectfully attached to carriage means 12 and supporting base means 13. Each of the cylinders 202 and 203 has a bore 204 that receives a hinge pin 205 as seen in FIG. 1. Disposed at the foot 47 of the bed 11 is a foot stand 210 to facilitate a patient in getting onto and off of bed 11. Carriage means 12 is pivoted about pivot axis 29 by one or more actuation means 211 that are pivotally attached at one end to a transverse support rail 212 extending between upright pedestals 15 and 16 and at the other end to carriage means 12.

Transverse rail support 212 forms part of previously referred to support structure 27. Structure 27 further includes stub rails 220 and 221 that extend substantially horizontally toward each other from pedestals 15 and 16 respectively. An upright support 222 extends between transverse rail 212 and the end of stub rail 220 while an upright support 223 extends between rail 212 and the end of stub rail 221. Upright rails 222 and 223 are space apart to define a gap 224 through which depending member 108 to which actuator 103 is attached extends when table 10 is pivoted into the patient access position.

The overall structure of distraction table 10 having been described, its various motions useful in facilitating the application of a therapeutic force to the spine of a patient will now be described as well as additional features of the distraction table 10 with particular reference to FIGS. 7-9.

Figure 7:
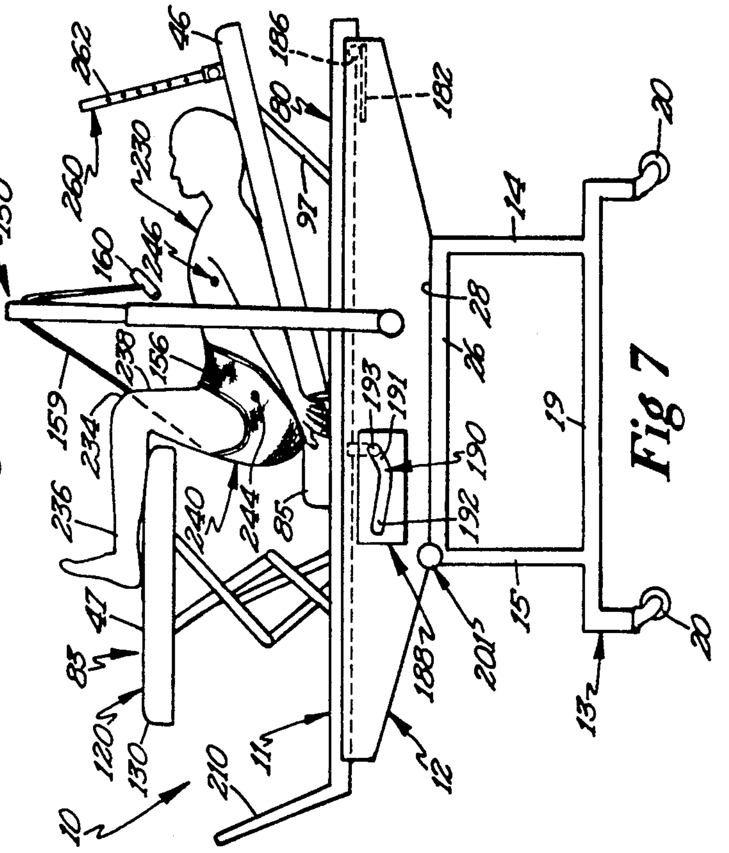
FIG. 7 is an operative, schematic view of a patient disposed on the table in an 90/90 position for distraction shown in FIG. 1.

Prior to being positioned on distraction table 10, a patient, indicated in FIGS. 7-9 with reference numeral 230, will have harness 156 attached. Generally, harness 156 has a three-lobed configuration known in the art with two of the three lobes encircling the waist and attaching to each other and the third extending from the back between the legs and upwardly therefrom. The third lobe includes a ring to which a hook 232 attached to cord 159 may be attached. Then, after pivoting of carriage means 12 and thus bed 11 about pivot axis 29 with respect to supporting base 13 through an arc of approximately 70° to a patient access position 199 as shown in FIG. 3. When so pivoted, bed 11 is in a generally upright position and foot stand 210 is substantially horizontally disposed and thus is substantially parallel with the floor. The patient is thus able to step onto stand 210, lean rearwardly against bed 11, and then be lowered into a supine position as carriage means 12 is pivoted back to the horizontal position shown generally in the Figures.

After bed 11 has been returned to the horizontal, the patient 230 will be attached to the means for lifting and rotating 150 via the harness 156, which is attached to hook 232. Lower leg portion 83 of bed 11 will be raised to its elevated operative position 120 and stool 130 will be translated forwardly so that the patient's knees, indicated generally by reference numeral 234, will be moved toward the head such that the lower leg 236 and upper leg 238 will form an angle slightly less than exactly ninety degrees, that is, the knees 234 will be closer to foot 47 of bed 11 than will the patient's buttocks; upper torso portion 82 will be pivoted to its operative position 100; and the patient's pelvic area, indicated generally by numeral 240, will be raised so that the patient's buttocks are about one half inch off of pelvic portion 85 by pulling on handle 160. In this position, a portion of the patient's body weight will be supported upwardly from bed 11 by harness 156 and its attachment to cross-piece 155, generally in the area of about twenty per cent of the patient's body weight, though such percentage will vary widely depending upon the physique of the particular patient. Means 150 may include a load cell 242 or other instrumentation means to indicate the weight supported thereby. The patient 230 will now be disposed in a 90/90 position for distraction of the spine. As seen in FIG. 7, rollers 186, 187 at the head of table 10 are near the beginning of their respective tracks 180, 181 and rollers 193, 194 are disposed at the beginning of the first segment 191 of force application path 190. In this position, the center of gravity 244 of the pelvic area of the patient 230 will be disposed lower than that of the center of gravity 246 of the torso region.

Referring now to FIG. 8, actuation means 195 has moved bed 11 along force application path 190, lowering pelvic portion 85 away from the patient 230 and opening a larger gap, indicated by reference numeral 248 between the pelvic area 240 and pelvic portion 85 than the one half-inch previously provided by raising the pelvic area 240 by means for lifting and rotating 150. As bed 11 translates, some of the patient's body weight will be transferred from the upper torso portion 84 to the means for lifting and rotating 150. This will raise the center of gravity 244 of pelvic area 240 relative to center of gravity 246 of the torso region above the pelvic area. In addition, a distraction force 250 will be directed along the axis of the straightened spine in a direction from the patient's head to his foot. Thus, even though cord 159 is attached to harness 156 and pulling thereon in a generally upward and foot to head direction, the pull exerted on the spine by the harness will be in a head to foot direction. Generally, the additional weight or pull indicated by load cell or instrumentation means 242 should be in the range of about two to twelve pounds or about a maximum of twenty-five percent of the weight of the elevated pelvic area. When this increased load is indicated, translation of bed 11 should cease to allow the distraction force 250 to slowly warm and stretch the connective tissue of the spine.

About 90 to 120 seconds after movement stops, the connective tissue will have plastically, that is, permanently elongated, thereby lowering pelvic area 240 back toward bed 11 as indicated in FIG. 9. Thus, FIG. 9 shows the patient after the spinal tissue has plastically stretched to lower the buttocks towards bed 11. When instrumentation means 242 indicates that means 150 is again supporting the weight originally raised off bed 11, translation of bed 11 along force application path 190 can again begin. In this manner, the connective tissue in the spinal area will be progressively elongated in a series of individual stretching steps to provide permanent relief. If desired, a patient activated switch may be provided to being and end the relative movement to avoid overly stressing a particular patient.

Force application track 190 functions to keep the applied force to the straightened spine directed substantially therealong. The substantially V-shaped configuration provided by path segments 191 and 192 facilitate this by keeping the straightened spine aligned with the direction of pull placed on the spine by means 150 as table 10 translates. It should be noted that the head 46 of table 10 follows a substantially horizontal path as the foot 47 thereof initially drops and then rises as the table moves rearwardly.

Also shown in FIGS. 3, and 7-9 is a cervical traction apparatus 260 including an upright, height adjustable member 262 attached to carriage means 12. A cervical harness 264 may be attached to upright member by a cord 266 and used to provide cervical traction as bed 11 translates. Alternatively, means 150 may be pivoted forwardly and harness 264 attached thereto to provide cervical traction. When both harness 156 and cervical harness 264 are attached as shown in FIG. 9, a traction force can be safely and effectively isolated in the thoracic segment of the spine. Table 10 is thus capable of providing a traction force in the lumbar, thoracic, and cervical spine areas.

The supporting structure of table 10 is preferably made of stainless steel, though other materials are within the purview of the present invention so long as they provide the stable support base needed for therapeutic applications. Also, more or less cross-bracing can be used to form bed 11, carriage means 12, and supporting base 13 as desired to facilitate the notions described herein and to provide a stable structure.

Actuators 97, 103, 131, 168, 211 and, in particular, actuator means 195, are preferably linear or screw drive actuators of the type manufactured by Raco International. Each of the aforesaid actuators may also be an hydraulic cylinder actuated by a fluid such as oil or air (pneumatic) if desired. The linear or screw type of actuation means is preferred over the fluid actuated hydraulic cylinder because it is not subject to messy leakage as can be the case where oil is used and because it is less subject to painful jerking motions as can happen where pneumatic cylinders are used. Particularly with respect to the latter factor, it is preferred that actuator means 195, which is used to translate bed 11, be a screw drive type of actuator since jerking of bed 11 during a treatment session could be painful for a patient.

Alternatively to using pivotable upper torso portion 84, a wedge like that shown in U.S. Pat. No. 4,602,619 may be used to position the upper torso of the patient. Also, in lieu of elevatable and translatable lower portion 85, a positioning stool such as that manufactured by Lossing Orthopedic, Inc., the assignee of the present invention, may be used to place the patient in the 90/90 position.

The distraction table 10 described above provided for a relative movement of the bed 11 relative to means 150 by translating bed 11. Alternatively, means 150 may be movable relative to a fixed patient bed along a similar, but reversed and inverted, force application path as path 190. With such an embodiment, means 150 would follow a first upwardly inclined path segment in a direction from the foot of the bed to the head thereof and a second downwardly inclined path segment in the same direction.

In addition to a clinical setting, the present invention may be used elsewhere. For example, the present invention may find use in the home setting as a home traction device that provides the relative movement described and set forth in the claims to achieve a spinal distraction and its therapeutic benefits.

The present invention having thus been described, other modifications, alterations, or substitutions may now suggest themselves to those skilled in the art, all of which are within the spirit and scope of the present invention. It is therefore intended that the present invention be limited only by the scope of the attached claims below.

I claim:

1. Apparatus for treating the spine of a patient, said apparatus comprising:

a carriage;

means for supporting the patient in a 90/90 position, said means for supporting including a bed;

means for lifting and rotating the pelvic region of the patient such that the lumbar portion of the spine is straightened, said means for lifting and rotating generally carrying the weight of the pelvic region of the patient while said means for supporting generally carries the remainder of the body weight of the patient; and means for selectively providing relative substantially translational motion between said means for supporting and said means for lifting and rotating such that a portion of the patient's body weight carried by said means for supporting is transferred from said means for supporting to said means for rotating and lifting and such that the patient's buttocks are raised off said means for supporting, wherein the transferred weight acts as a traction force applied to the spine to therapeutically and selectively elongate the spine;

wherein said bed includes a head and a foot and said relative substantially translational movement includes movement of said bed along a path in a head to foot direction, said path including a first path segment having a generally downwardly inclined direction.

2. The apparatus of claim 7 wherein said transferred weight is in the range of about two to twelve pounds.

3. The apparatus of claim 1 wherein said means for lifting and rotating includes means for determining the weight of the pelvic region and the transferred body weight.

4. The apparatus of claim 1 wherein the torso region of the patient above the pelvic region is carried by said means for supporting and wherein the pelvic region of the patient and the torso region of the patient above the pelvic region are moved relative to one another by said relative motion of said means for supporting and said means for lifting and rotating.

5. The apparatus of claim 4 wherein the pelvic region and the torso region of the patient each have respective centers of gravity and wherein prior to said relative motion the pelvic region center of gravity and the torso region center of gravity are disposed in a first position by said means for supporting and said means for lifting and rotating such that the torso region center of gravity is elevated above the pelvic region center of gravity, said relative motion of said means for supporting and said means for lifting and rotating disposing the torso region and the pelvic region in a second position in which the torso region center of gravity and the pelvic region center of gravity have a lesser relative elevation difference than the torso region and the pelvic region have in said first position.

6. The apparatus of claim 1 wherein said first path segment is inclined at an angle of about 14½ degrees with respect to the horizontal.

7. The apparatus of claim 1 wherein said path includes a second path segment having a generally upwardly inclined direction.

8. The apparatus of claim 7 wherein said second path segment is inclined at an angle of about 9½ degrees with respect to the horizontal.

9. The apparatus of claim 7 wherein said first path segment is inclined at an angle of about 14½ degrees with respect to the horizontal and said second path segment is inclined at an angle of about 9½ degrees with respect to the horizontal.

10. The apparatus of claim 7 wherein said means for providing said relative motion includes a screw drive attached at one end to said bed and at the other end to said carriage.

11. The apparatus of claim 1 wherein said bed includes a foot portion and a torso portion and wherein said means for supporting further includes:

means for elevating said torso portion of said bed at an angle to the horizontal;

means for elevating said foot portion of said bed such that the patient is substantially disposed in said 90/90 position, said means for elevating includes a scissors lift mechanism; and means for translational movement of said foot portion in a head/foot direction when said foot portion is elevated.

12. The apparatus of claim 11 including means for substantially horizontal movement of said foot portion in a forward/rearward direction when said foot portion is elevated.

13. The apparatus of claim 11 wherein said means for elevating includes a scissors lift mechanism.

14. The apparatus of claim 11 wherein said means for supporting further includes means for elevating said torso portion of said bed at an angle to the horizontal.

15. The apparatus of claim 1 wherein said bed includes foot and torso portions, said torso portion of said bed being pivotal with respect to said foot portion and wherein said means for supporting further includes:

means for elevating said torso portion from a first position to a second position at an angle to said first position such that the torso region of the patient above the pelvic region is moveable from a first torso position to a second torso position, wherein said second torso position is at an angle with respect to said first torso position.

16. The apparatus of claim 15 wherein said first torso position is substantially horizontal.

17. The apparatus of claim 7 wherein said means for supporting includes wedging means for disposing the torso region of the patient above the pelvic region of the patient at an angle with respect to the horizontal.

18. The apparatus of claim 1 wherein said bed includes a foot plate disposed substantially perpendicularly to said bed, said bed having a substantially horizontal disposition when not in use and wherein said means for supporting further includes:

means for pivotally tilting said bed to a generally upright position for easy access by the patient;

whereby said bed may be tilted to a substantially upright position such that the patient may access said bed substantially without bending his injured spine by stepping onto said foot plate and by being supported by said foot plate and said bed during access and whereby said bed may be tilted back to said horizontal position for said relative motion.

19. Apparatus for treating the spine of a patient, said apparatus comprising:

a carriage;

means for supporting the patient in a 90/90 position, said means for supporting including a bed;

means for lifting and rotating the pelvic region of the patient such that the lumbar portion of the spine is straightened, said means for lifting and rotating generally carrying the weight of the pelvic region of the patient while said means for supporting generally carries the remainder of the body weight of the patient; and means for selectively providing relative substantially translational motion between said means for supporting and said means for lifting and rotating such that a portion of the patient's body weight carried by said means for supporting is transferred from said means for supporting to said means for rotating and lifting and such that the patient's buttocks are raised off said means for supporting, wherein the transferred weight acts as a traction force applied to the spine to therapeutically and selectively elongate the spine;

wherein said bed is movably supported by said carriage and said means for lifting and rotating is attached to said carriage and includes:

an elongate arm pivotally attached at one end thereof to said carriage and extending generally upwardly therefrom;

a cross-piece attached to the other end of said arm, said cross-piece extending generally horizontally over said bed;

a harness for encircling the pelvic region of the patient, said cross-piece supporting said harness; and means for varying the height of said harness relative to said bed;

wherein said harness is attached to the pelvic region of the patient and the pelvic region of the patient is elevated from and raised above said bed by said means for varying.

20. The apparatus of claim 19 wherein said means for providing said relative motion includes a screw drive for moving said arm relative to said bed.

21. Apparatus for treating the spine of a patient, said apparatus comprising:

a carriage;

means for supporting the patient in a 90/90 position, said means for supporting including a bed;

means for lifting and rotating the pelvic region of the patient such that the lumbar portion of the spine is straightened, said means for lifting and rotating generally carrying the weight of the pelvic region of the patient while said means for supporting generally carries the remainder of the body weight of the patient; and means for selectively providing relative substantially translational motion between said means for supporting and said means for lifting and rotating such that a portion of the patient's body weight carried by said means for supporting is transferred from said means for supporting to said means for rotating and lifting and such that the patient's buttocks are raised off said means for supporting, wherein the transferred weight acts as a traction force applied to the spine to therapeutically and selectively elongate the spine;

wherein said means for lifting and rotating is movably supported by said carriage and includes;

an elongate arm pivotally attached at one end thereof to said carriage and extending generally upwardly therefrom;

a cross-piece attached to the other end of said arm, said cross-piece extending generally horizontally over said bed;

a harness for encircling the pelvic region of the patient, said cross-piece supporting said harness; and means for varying the height of said harness relative to said bed;

wherein said harness is attached to the pelvic region of the patient and the pelvic region of the patient is elevated from and raised above said bed by said means for varying; and wherein said bed includes a head and a foot and said arm is movable along a path relative to said bed in a foot to head direction, said path having a first path segment in a generally upwardly inclined direction.

22. The apparatus of claim 21 wherein said first path segment is inclined at an angle of about 9½ degrees with respect to the horizontal.

23. The apparatus of claim 21 wherein said path includes a second path segment having a generally downwardly inclined direction.

24. The apparatus of claim 23 wherein said second path segment is inclined at an angle of about 14½ degrees with respect to the horizontal.

25. The apparatus of claim 23 wherein said first path segment is inclined at an angle of about 9½ degrees with respect to the horizontal and said second path segment is inclined at an angle of about 14½ degrees with respect to the horizontal.

26. A method for treating the injured spine of a patient comprising:

placing the patient in a 90/90 position;

elevating and rotating the pelvic region of the patient wherein the spine tends to straighten; and applying a predetermined traction force to said spine to therapeutically treat the spine by selectively transferring body weight to the pelvic region of the patient;

wherein the body weight is transferred by selectively moving the torso region of the patient downwardly and toward the elevated and rotated pelvic region.

27. The method of claim 26 wherein said traction force is less than about twenty-five percent of the weight of the elevated and rotated pelvic region.

28. The method of claim 27 and further including:

providing instrumentation means for determining the weight of the elevated pelvic region and the applied traction force; and applying a traction force at a predetermined rate until said predetermined traction force is fully applied.

29. The method of claim 29 wherein the connective tissue in the patient's spine elongates as said predetermined traction force is applied, said traction force declining as the connective tissue elongates.

30. The method of claim 29 wherein said predetermined traction force is applied a successive plurality of times in each treatment session, each successive traction force being applied at the end of the previous elongation of said connective tissue.

31. Apparatus for applying a traction force to the spine of a patient to provide a therapeutic treatment thereof, said apparatus comprising:

a carriage defining in part a force application path;

means for supporting the patient in a 90/90 position, said means for supporting being attached to said carriage;

means for lifting and rotating the pelvic region of the patient such that the spine is straightened, said means for lifting and rotating providing a fixed reference point relative to the patient for application of the traction force, said means including a harness for encircling the pelvic region of the patient; and actuation means for selectively moving said means for supporting relative to said means for lifting and rotating along said force application path such that said means for supporting is moved relative to said fixed reference point and such that the patient's buttocks are elevated above said means for supporting and such that a traction force is applied to the spine of the patient;

wherein:

said means for supporting includes a bed movably supported by said carriage and is movable along said force application path by said actuation means, wherein said bed includes a head and a foot and said bed is movable along said force application path in a head to foot direction, said path including a first path segment having a generally downwardly inclined direction; and means for lifting and rotating is attached to said carriage.

32. The apparatus of claim 31 wherein said first path segment is inclined at an angle of about 14½ degrees with respect to the horizontal.

33. The apparatus of claim 31 wherein said force application path includes a second path segment having a generally upwardly inclined direction.

34. The apparatus of claim 33 wherein said second path segment is inclined at an angle of about 9½ degrees with respect to the horizontal.

35. The apparatus of claim 33 wherein said first path segment is inclined at an angle of about 14½ degrees with respect to the horizontal and said second path segment is inclined at an angle of about 9½ degrees with respect to the horizontal.

36. The apparatus of claim 31 wherein said means for supporting includes:

a bed supported by said carriage; and wherein said means for lifting and rotating includes:

an elongate arm pivotally attached at one end thereof to said carriage and extending generally upwardly therefrom;

a cross-piece attached to the other end of said arm, said cross-piece extending generally horizontally over said bed;

a harness for encircling the pelvic region of the patient, said cross-piece supporting said harness; and means for varying the height of said harness relative to said cross-piece;

wherein said harness is attached to the pelvic region of the patient and the pelvic region of the patient is elevated from and raised above said bed by said means for varying.

37. The apparatus of claim 36 wherein said bed includes a head and a foot and said arm is movable along said force application path in a foot to head direction, said force application path having a first path segment in a generally upwardly inclined direction.

38. The apparatus of claim 37 wherein said first path segment is inclined at an angle of about 9½ degrees with respect to the horizontal.

39. The apparatus of claim 37 herein said force application path includes a second path segment having a generally downwardly inclined direction.

40. The apparatus of claim 39 wherein said second path segment is inclined at an angle of about 14½ degrees with respect to the horizontal.

41. The apparatus of claim 39 wherein said first path segment is inclined at an angle of about 9½ degrees with respect to the horizontal and said second path segment is inclined at an angle of about 14½ degrees with respect to the horizontal.

42. The apparatus of claim 31 and further including means for applying traction to the cervical area of the spine.

43. The apparatus of claim 42 wherein said relative movement produces traction of the thoracic spine of the patient.

44. Apparatus for applying a traction force to the spine of a patient to provide a therapeutic treatment thereof, said apparatus comprising:

a carriage defining in part a force application path;

means for supporting the patient in a 90/90 position, said means for supporting being attached to said carriage;

means for lifting and rotating the pelvic region of the patient such that the spine is straightened, said means for lifting and rotating providing a reference point relative to the patient for application of the traction force, said means including a harness for encircling the pelvic region of the patient; and actuation means for selectively moving said means for lifting and rotating relative to said means for supporting along said force application path such that the patient's buttocks are elevated above said means for supporting and such that a traction force is applied to the spine of the patient;

wherein:

said means for supporting includes a bed, said bed including a head and a foot; and said means for lifting and rotating is movably supported by said carriage and is movable along said force application path by said actuation means in a foot to head direction, said path including a first path segment having a generally upwardly inclined direction.

* * * * *

UNITED STATES PATENT AND TRADEMARK OFFICE

CERTIFICATE OF CORRECTION

PATENT NO. : 5,308,359

DATED : May 3, 1994

INVENTOR(S) : Wallace W. Lossing

It is certified that error appears in the above-indentified patent and that said Letters Patent is hereby corrected as shown below:

In col. 8, line 59, delete "Unshaped" and substitute --U-shaped-- therefor.

In col. 9, line 52, delete "Unshaped" and substitute --U-shaped-- therefor.

In col. 12, line 24, delete "being and substitute --begin-- therefor.

In claim 2, col. 13, line 65, delete "7" and substitute --1-- therefor.

In claim 29, col. 17, line 18, delete "29" and substitute --26-- therefor.

In claim 39, col. 18, line 32, delete "herein" and substitute --wherein-- therefor.

UNITED STATES PATENT AND TRADEMARK OFFICE

CERTIFICATE OF CORRECTION

PATENT NO. : 5,308,359

DATED : May 3, 1994

INVENTOR(S) : Wallace W. Lossing

It is certified that error appears in the above-indentified patent and that said Letters Patent is hereby corrected as shown below:

In claim 17, col. 15, line 10, delete "7" and substitute --1-- therefor.

Signed and Sealed this

Twenty-eighth Day of November 1995

Attest:

BRUCE LEHMAN

*Attesting Officer*

*Commissioner of Patents and Trademarks*